United States Patent [19]

Coleman, Sr.

[11] Patent Number: 5,709,904
[45] Date of Patent: Jan. 20, 1998

[54] SYSTEM FOR MANUFACTURING CHROMATOGRAPHIC COLUMNS

[75] Inventor: David W. Coleman, Sr., Wilmington, Del.

[73] Assignee: C&C Column Technologies, Inc., Oxford, Pa.

[21] Appl. No.: 680,450

[22] Filed: Jul. 15, 1996

[51] Int. Cl.⁶ ........................................ B05D 7/22
[52] U.S. Cl. ................... 427/8; 427/230; 427/399.7
[58] Field of Search ........................ 427/230, 389.7, 427/8

[56] References Cited

U.S. PATENT DOCUMENTS

| | | |
|---|---|---|
| 3,547,684 | 12/1970 | Hollis et al. ............................ 427/230 |
| 4,054,432 | 10/1977 | Taylor et al. ........................... 427/230 |
| 4,293,415 | 10/1981 | Bente, III et al. ..................... 210/198.2 |
| 4,509,964 | 4/1985 | Hubball et al. ........................ 55/386 |
| 4,726,822 | 2/1988 | Cates et al. ........................... 55/267 |
| 4,966,785 | 10/1990 | Springston ............................. 427/230 |
| 5,145,579 | 9/1992 | Eguchi et al. ......................... 210/198.2 |

*Primary Examiner*—Janyce Bell
*Attorney, Agent, or Firm*—William B. Noll

[57] ABSTRACT

Invention is directed to a system, i.e. method and apparatus, for manufacturing thin-walled capillary columns for use in a gas chromatographic device. The system involves the sequential filling and evacuating of the columns in a controlled environment, where the system is under the control of a microprocessor to achieve improved processing control and monitoring. The system also produces a consistant homogeneous film of polymer along the inner wall of the columns.

9 Claims, 3 Drawing Sheets

SYSTEM FOR MANUFACTURING CHROMATOGRAPHIC COLUMNS

FIELD OF INVENTION

This invention relates to the field of high resolution gas chromatography, the science of gas-liquid separation, i.e. partitioning of a component between two phases. More specifically, the invention hereof is directed to a unique system for manufacturing fine, thin-walled, capillary columns, the major component used in the oven of a gas chromatographic system.

BACKGROUND OF THE INVENTION

The present invention relates to an improved system for the automated coating and fixing of thin-walled capillary columns for use in a gas chromatograph, where a sample material may be introduced into one end and emerge at the other end at different times, hence a separation.

U.S. Pat. No. 4,293,415, the contents of which are incorporated herein by reference, in its entirety, represents the current state of the art in the development of fused silica capillary columns. Prior to such development, chromotography columns had been produced from glass. However, such columns had certain inherent disadvantages. They were fragile and easily broken if overstressed. Additionally, glass columns distorted peak shapes of sample materials that are either too acidic or too basic. For example, this effect may be caused by such samples which adsorb strongly to the gas surface, causing the sample components not to elute from the column or to elute with peak shapes seriously distorted from the traditional symmetrical shape.

U.S. Pat. No. '415, recognized that flexible capillary columns could be produced from fused silica. By way of further background, it was discovered that a large hollow tube of fused silica could be drawn to produce a column with a typical outside diameter of 0.8 mm. and an inside diameter of about 0.25 mm., and which could be readily manipulated by hand. Thereafter, a coating of a polymer or metal was applied to the exterior surface so as to protect the silica tube from abrasion and moisture. Protection from abrasion is necessary because the slightest scratch could cause the tube to break when stressed, and protection from moisture is necessary because over a period of time moisture can weaken the surface of the tube until it breaks when stressed.

Because gas chromatography columns are used in controlled temperature ovens at temperatures which may be as high as 350 degrees C. or higher, the protective coating on the outside is a material which is stable with respect to decomposition or oxidation at these temperatures. Materials such as polyimide or silicone rubber polymers, or metals, such as aluminum or nickel, are suitable coatings. Protection from moisture can also be achieved by depositing a layer of silicone nitride on the outside surface of the silica, however this intermediate coating is generally coated with a layer of polymer or a deposited metal to provide protection from abrasion.

The internal surface of the silica tube, through which the sample material passes, is typically coated with a stationary sample in the form of a crosslinked and/or bonded polymer. Thus, in the case of U.S. Pat. No. '415, the final product is a flexible hollow tube of drawn fused silica, of thin-wall construction, having an inner surface of a stationary phase material, and an outer surface with a moisture and abrasion resistant coating.

U.S. Pat. No. 4,509,964 represents a different approach to treating the inner surface of a fused silica capillary column. Specifically, the approach thereof comprises the steps of irradiating the inner wall with gamma radiation, followed by applying a polar stationary phase to the thus treated inner wall, to improve wettability of the wall surface.

U.S. Pat. No. 4,726,822 offers a further element to a fused silica column in the form of a heater film or layer. Specifically, the silica column includes a high temperature chemically inert polymer coating supporting a thin heater film formed by the deposition of either a high resistance metallic compound auto-catalyically from a solution of the compound or a nichrome film sputtered onto the polymer clad capillary tubing. An advantage thereof is the ability to use such columns in a portable field analyzer.

Despite the introduction of fused silica columns, first noted in an article entitled, The Origination, Development and Potentialities of Glass Capillary Columns" at p. 452, September 1975 issue of Chromatographia, V. 8, No. 9, glass columns were still in use fifteen years later. In U.S. Pat. No. 5,145,579, there is taught a method for the manufacture of a glass separation column. The method thereof includes the step of selecting a glass capillary coated with a polymer film on the inside having an internal diameter of maximally 10 p and having a ratio between the volume of the polymer film and the internal volume of the capillary after the film has been applied larger than 0.14. Thereafter the method concludes with the steps of silylating the inside of the capillary, filling the capillary with a solution of a photo initiator and/or thermal initiator and acrylate monomers and/acrylate oligomers in a solvent, polymerizing the monomers in situ by means of UV or visible light or by heating, evaporating the solvent while forming the resultant polymer film and thermally postcuring the polymer film.

While even the later development of fused silica has been known for years, there does not appear to be a recorded system for automating the manufacture of thin-walled columns for use in a chromatographic system. The present invention sets forth a microprocessor driven system, i.e. method and apparatus, to effectively and precisely manufacture such columns. The manner by which this system achieves its results will become apparent in the description which follows, particularly when read in conjunction with the accompanying drawings.

SUMMARY OF THE INVENTION

This invention is directed to an improved system, i.e. method and apparatus, for the automated coating and fixing of thin-walled columns, such as fused silica or metal. An exemplary starting product for the method, though not limiting, may be a fused silica capillary tube, of predetermined length, having a polyimide coating on the external surface. Conventional capillary tubes suitable for practicing this invention typically have an O.D. of between about 0.50 to 0.80 mm. with a complimentary I.D. of between about 0.25 to 0.53 mm. The method, a microprocessor driven procedure, includes the steps of metering a quantity of a polymer, under pressure, through said tube; sealing one end of the tube, and evacuating the tube, under vacuum, to leave a homogeneous film of said polymer along the inner surface thereof; crosslinking the film in a heated bath; and rinsing the internally coated tube. Thereafter as a final step, the coated and rinsed tube or capillary column is conditioned trader the application of heat in a controlled environment.

BRIEF DESCRIPTION OF DRAWINGS

FIG. 2 is a partial schematic diagram for the column filling operation, while FIG. 3 is a partial schematic diagram for the column evacuating operation.

DETAILED DESCRIPTION OF PREFERRED EMBODIMENT

This invention is directed to a system for manufacturing capillary columns for use in high resolution gas chromatographic apparatus. Such columns, as known in the art, are thin-walled tubes of predetermined length with an I.D. in the range of from 0.25 to 0.53 mm., an O.D. of from 0.50 to 0.80 mm., and are conventionally produced from fused silica. Though the present invention is applicable to fused silica and other thin-walled capillary tubing, such as metal, preferably aluminum and stainless steel, the further description of a preferred embodiment, for convenience, will be limited to fused silica.

In the practice of this invention, a preferred starting material or product is a thin-walled silica column, with an I.D. of about 0.25 mm., an O.D. of about 0.66 mm., having an abrasion and moisture resistant coating, such as polyimide. However, one advantage of a metal capillary column is that no further external coating is required.

Figure 1:
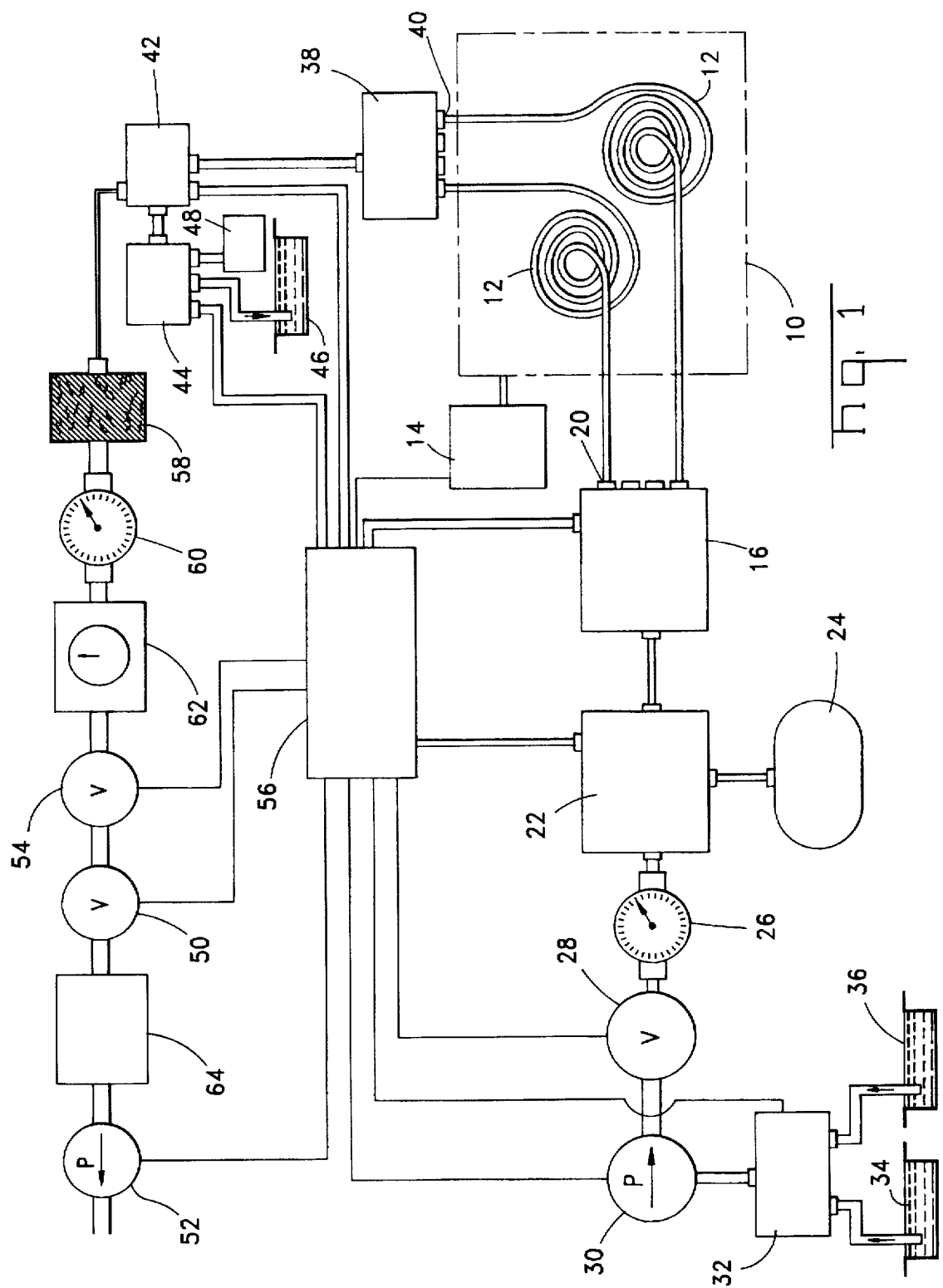
FIG. 1 is a schematic diagram of the apparatus for filling and evacuating one or more thin-walled capillary columns to prepare same for use in a chromatographic device.

The system hereof is to transform such starting material into a chromatographic column by coating and fixing a polymeric coating along the internal surface thereof. This transformation is accomplished by the apparatus schmetically illustrated in the several Figures, where FIG. 1 shows the full system. As will be apparent in the further description of said Figures, there are two primary operations in the manufacture of the columns: filling and evacuating. The filling operation is depicted in FIG. 2, while FIG. 3 shows the evacuating operation.

Figure 2:
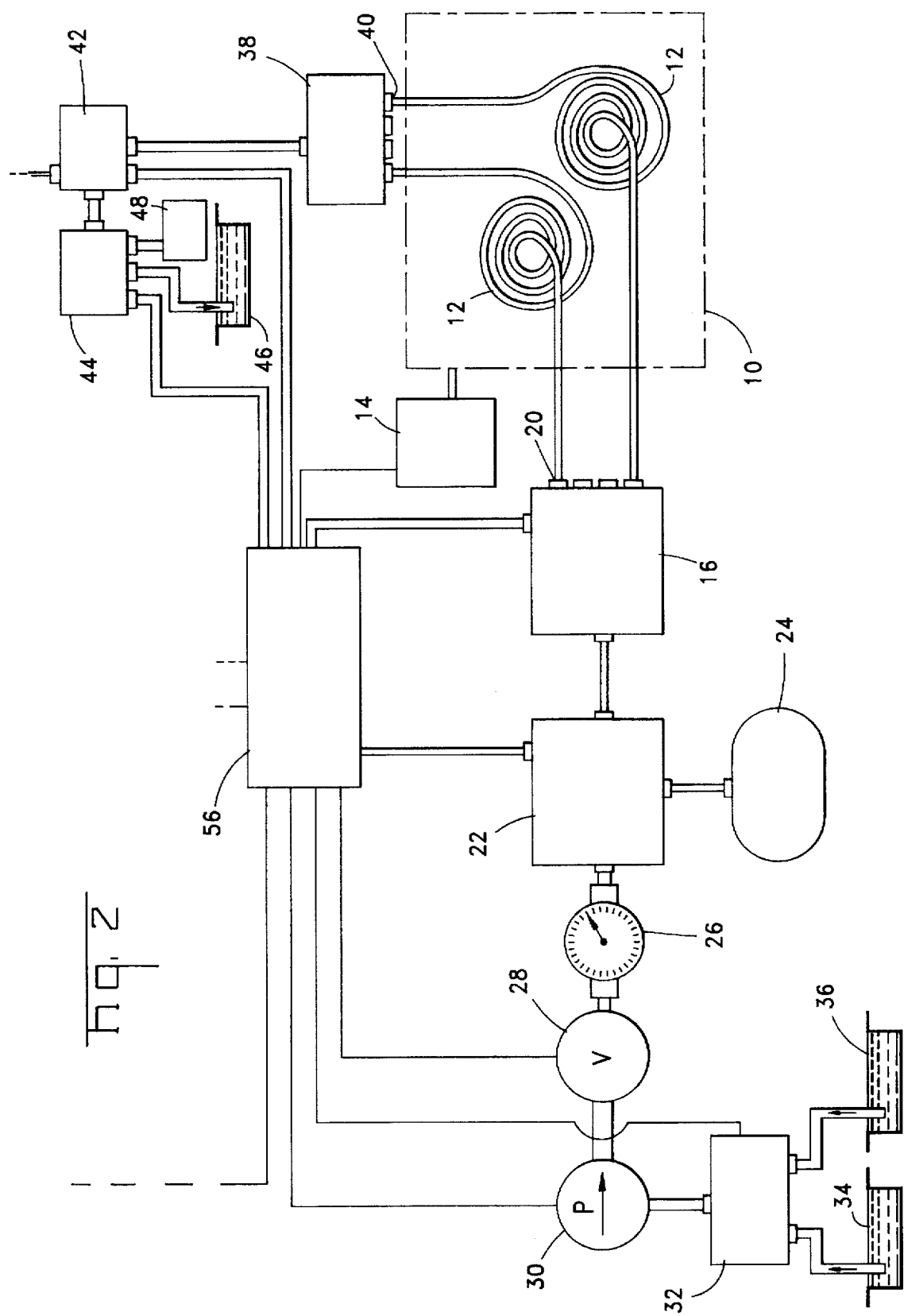
Figure 7:
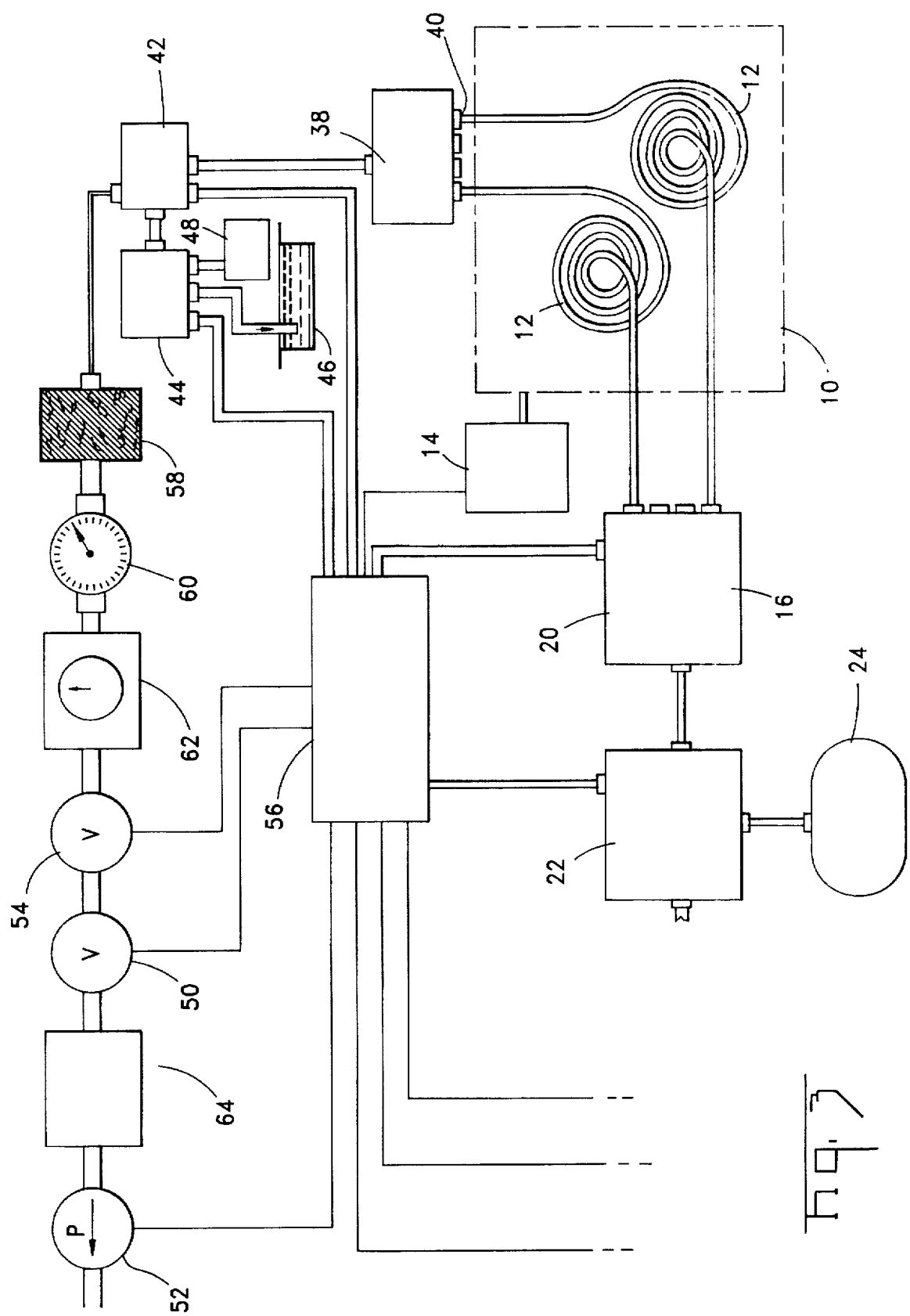

Turning first to the filling operation of FIG. 2, there is illustrated a heating bath 10 into which the column(s) 12, typically in coil form, are placed. The bath consists of a liquid, preferably capable of reaching and sustaining temperatures up to about 200 degrees C., the purpose of which will become apparent hereafter. While various means may be employed to raise and maintain the bath temperature as described later, a heater/circulator 14 is a convenient means. Adjacent the bath 10 is a multiposition sealing valve 16, which for this illustration shows four ports 18 to which respective ends 20 of the columns 12 are releasibly but sealingly engaged. An exemplary multiposition sealing valve 16 suitable for practicing this invention is manufactured by Valco Instruments Co., Inc., of Houston, Tex., under model No. EMTMA. Continuing with the operation, feeding into said multiposition sealing valve 16 is a second multiposition valve 22, including a gas supply 24, such as for a purging gas like nitrogen. Continuing upstream, there may be provided a pressure guage 26, primarily for safety reasons to ensure proper pressure for the selected columns and their arrow internal diameters, a manual two-way valve 28 for waste, i.e. polymer by-pass during column filling, and a metering pump 30. Leading to the motoring pump 30 is a two-position, microprocessor controlled valve 32, such as an electrically activated valve, directing either the coating polymer solution from a first reservoir 34, or rinse solution from a second reservoir 36.

The filling operation follows the reverse or down stream flow from the first reservoir 34 through the multiposition sealing valve 16 with the coating polymer solution entering into the one or more columns 12. As the polymer flows through the columns 12, the polymer continues into a multiport column manifold 38, where the opposite ends 40 of the columns 12 have been releasably secured. Thereafter, the polymer solution continues to a two-position, microprocessor controlled valve 42, thence to a final two-position, microprocessor controlled valve 44, and released into a waste reservoir 46. Note also that the final two-position, microprocessor controlled valve 44 includes a gas supply 48 for back pressurizing as hereinafter explained.

Once the filling operation has been completed, conversion to the evacuating operation may begin. However, optionally a rising operation may be injected here following the basic coating or filling operation, or preferably after the crosslinking step, as hereafter noted, where the rinse solution is taken from the second reservoir 36 with the overflow of waste exiting into the waste reservoir 46, whereby to remove impurities, volatives, and undissolved polymers. Additionally, the system may be purged, such as by nitrogen, from gas supply 24. In any case, thereafter, as a first step in the evacuating process, second multiposition valve 22 is switched to block or seal and further down stream flow of the polymer solution is prevented. At this point, gas, such as nitrogen, is caused to reverse flow from gas supply 48 to back pressure the columns 12 and trap any undesirable particles and air between the valves 22, 16. With the system pressurized, multiposition sealing valve 16 is then switched to 'block', thus closing the trap. With multiposition sealing valve 16 closed, the evacuating operation may be initiated.

Since a further feature of the evacuating cycle or operation is to facilitate crosslinking of the polymer coating along the inner wall of the columns, the bath temperature is raised. Concurrently, the vacuum needle 50 is moved manually or automatically by operation of the microprocessor, as hereafter identified, to the full open position, then the system is brought to a full vacuum, by means of vacuum pump 52 by slowly closing the bleed valve 54. This may typically take a period of from 15 to 20 minutes. After evacuation to remove solvent, and leave a thin homogeneous inner polymer film of from about 0.1µ to 5.0µ, the bath temperature is raised and maintained, if required, at a temperature of about 70 degrees C. for about 1 hour to facilitate crosslinking of the polymer film. If desired, the columns 12 may be rinsed after crosslinking and purge dried with nitrogen. In any case, to condition the thus treated columns 12, the bath temperature is further elevated to a temperature of about 200 degrees C., where a suitable bath may consist of tetraethylene glycol and capable of sustaining temperatures in a safe environment, for about 1 to 2 hours. Thereafter, the vacuum may be released and the columns 12 removed for testing and eventual use in a chromatographic device. This operation is all accomplished under the control of microprocessor 56. An exemplary system for operating the microprocessor 56 may be the Microsoft Visual Basic system, a programming tool, as known in the art, which allows one to communicate with instruments.

For safety, and to ensure a proper working environment for the system, a filler 58, for example, is interposed between the two-position, microprocessor controlled valve 42 and a vacuum gauge 60. Essentially the filter 58 is a safely measure as a liquid trap in the event of breakage or a malfunction in the system. Further, under proper evacuation conditions, the vacuum gauge 60 would typically reveal a vacuum of about 27–28" mercury. Additionally, a mass flow meter 62 and solvent cold trap 64 may be provided.

While some variations or modifications may be made in the preferred apparatus, the process incorporates the following basic steps to achieve the preferred end product. As noted previously, such preferred process includes two integrated and sequentially controlled primary operations or cycles, namely, column filling and column evacuating.

"Column Filling"

The process begins by selecting one or more predetermined lengths of thin-walled, open ended capillary tube(s) which have been provided previously with an abrasion and moisture resistant external surface, namely, an applied coating or the inherent nature of the base product. Into such capillary tube(s) metered quantities, under pressure, of a polymer and solvent, containing a crosslinking agent, are passed through the tube(s), where an exemplary polymer is polydimethyl siloxane (1 to 5%) in an organic solvent, such as pentane.

"Column Evacuating"

To effect the evacuation of excess polymer from the tube(s), leaving a homogeneous film along the inner wall thereof, the tube(s) are closed upstream, i.e. the feeding end. The depth of the residual film, as known in the art, is dependent upon the ratio of the polymer to its solvent. A polymer solution of about 1% polydimethyl siloxane, for example, will produce a film of about 1.5μ thickness. With the tube(s) suitably sealed at one end, a vacuum is drawn from the other end of the tube(s). While the vacuum is maintained, heat may be applied to the tube(s) or column(s) to facilitate crosslinking of the polymer. Dicumyl peroxide, present in an amount of about 3 to 5%, by weight, of the polymer, is an exemplary crosslinking agent for practicing this invention. Though it is not common for isolated inner surface areas to remain uncoated, the tube(s) may optionally be subjected to a further and final conditioning step, and rinsing. While the crosslinked tube(s) are still under vacuum, the tube(s) are further heated and maintained at a temperature of about 200 degrees C. for a period of from 1 to 2 hours to condition the column. This process has major advantages over prior art practices in that the tube(s) or column(s) are fully processed in an environment that eliminates undesirable particles, avoids the incursion of contaminants into the columns during their manufacture, and minimizes manual handling of the columns while nearly eliminating the impact of human errors in the process.

I claim:

1. An automated method for the manufacture of thin-walled capillary columns for use in a chromatographic device, the steps comprising, a.) selecting a predetermined length of a thin-walled, open ended capillary tube having an abrasion and moisture resistant external surface, b.) metering a quantity of a polymer with a crosslinking agent, under pressure, through said tube, c.) sealing one end of said tube, and evacuating said tube, under vacuum, to deposit a homogeneous film of said polymer along the inner surface thereof, and, d.) maintaining said vacuum while crosslinking said film, whereby, steps (b) through (d) are sequentially coordinated through a microprocessor.

2. The automated method according to claim 1, including a further step of e.) conditioning the coated capillary column under the application of heat, which step is also coordinated through said microprocessor.

3. The automated method according to claim 2, wherein said homogeneous film is a uniform layer of about 0.1 to 5.0 u in thickness.

4. The automated method according to claim 2, wherein the crosslinking of said polymer is by the application of a heated bath while said tube is maintained under said vacuum.

5. The automated method according to claim 2, wherein said capillary tube is fused silica having a thin external coating of polyimide.

6. The automated method according to claim 2, wherein said capillary tube is a metal selected from the group consisting of aluminum, aluminum alloys, and stainless steel.

7. The automated method according to claim 2, wherein said conditioned tubes are subjected to a rinsing step.

8. The automated method according to claim 1, wherein the capillary tube is maintained in a protected environment during its manufacture, whereby to achieve improved processing control and monitoring.

9. The automated method according to claim 1, wherein said system achieves consistant reproducibility in said homogeneous film.

* * * * *